United States Patent
Hack et al.

(10) Patent No.: US 7,278,787 B2
(45) Date of Patent: Oct. 9, 2007

(54) X-RAY APPARATUS WITH POSITIONING MEASURES

(75) Inventors: Alexander Hack, Biberach (DE); Uwe Zeller, Biberach (DE); Klaus Weber, Grodt (DE); Martin Rickert, Bad Wurzach-Haidgau (DE)

(73) Assignee: Kaltenbach + Voigt GmbH (DE)

( * ) Notice: Subject to any disclaimer, the term of this patent is extended or adjusted under 35 U.S.C. 154(b) by 0 days.

(21) Appl. No.: 11/234,904

(22) Filed: Sep. 26, 2005

(65) Prior Publication Data

US 2006/0067483 A1 Mar. 30, 2006

Related U.S. Application Data

(63) Continuation of application No. PCT/EP2004/003128, filed on Mar. 24, 2004.

(30) Foreign Application Priority Data

Mar. 24, 2003 (DE) ............... 103 13 041
Oct. 6, 2003 (DE) ............... 103 46 288

(51) Int. Cl.
*A61B 6/08* (2006.01)
*A61B 6/14* (2006.01)
(52) U.S. Cl. .................. 378/206; 378/38; 378/170
(58) Field of Classification Search ............. 378/206, 378/38, 39, 145, 161, 168, 170, 205
See application file for complete search history.

(56) References Cited

U.S. PATENT DOCUMENTS 1,976,179 A * 10/1934 Mannl .................. 378/206
2,955,205 A    10/1960 Camfferman
3,092,721 A *  6/1963 Medwedeff et al. ....... 378/170
3,767,931 A   10/1973 Williams
4,012,638 A *  3/1977 Altschuler et al. ......... 378/170
5,553,115 A    9/1996 Odaka et al.
5,708,696 A    1/1998 Kantor
5,782,842 A *  7/1998 Kloess et al. ............ 606/130
6,229,873 B1 * 5/2001 Bani-Hashemi et al. ... 378/206
2002/0122537 A1 9/2002 Yoshimura

FOREIGN PATENT DOCUMENTS

FR    2384481    10/1978
FR    2614491    10/1988
WO    99/60928   12/1999

OTHER PUBLICATIONS

"Hand-held three-dimensional dental X-ray system: Technical description and preliminary results" by RL Webber et al.; Dentomaxillofacial Radiology, 2002, pp. 240-248.

* cited by examiner

*Primary Examiner*—Chih-Cheng G Kao
(74) *Attorney, Agent, or Firm*—Mayback & Hoffman, P.A.; Gregory L. Mayback; Scott D. Smiley

(57) ABSTRACT

An X-ray apparatus, in particular a dental X-ray apparatus, includes an X-ray radiation source for generating X-ray radiation to be directed at an object to be investigated, for example, a patient's tooth or jaw. The apparatus has an optical device through which an aiming device, for example, an additional visible pilot radiation generated by a further light source, is directed substantially parallel to the X-ray radiation at the object to be investigated to facilitate the positioning of the X-ray head.

26 Claims, 3 Drawing Sheets

X-RAY APPARATUS WITH POSITIONING MEASURES

CROSS-REFERENCE TO RELATED APPLICATION

This is a continuing application, under 35 U.S.C. § 120, of copending international application No. PCT/EP2004/003128, filed Mar. 24, 2004, which designated the United States; this application also claims the priority, under 35 U.S.C. § 119, of German Patent Application No. 103 13 041.1, filed Mar. 24, 2003 and of German Patent Application No. 103 46 288.0, filed Oct. 6, 2003; the prior applications are herewith incorporated by reference in their entirety.

BACKGROUND OF THE INVENTION

Field of the Invention

The present invention relates to an X-ray apparatus, in particular, an X-ray apparatus that is employed in dental diagnosis.

For a complete and accurate diagnosis in dental medicine, the use of dental X-ray apparatuses is essential. Thus, faulty positioning of teeth or damage to the teeth in the root region can be diagnosed with high accuracy and dependability only based upon dental X-ray images.

X-ray techniques that are put to use may, in substance, be divided into two different categories.

In the case of a so-called intraoral X-ray exposure, an X-ray radiation sensitive sensor, either an X-ray film or a digital sensor in the form of a semiconductor sensor located in a housing, is brought into the mouth of the patient and X-ray radiation is directed from the exterior at the region to be investigated. The sensors brought into the mouth have dimensions in the range of a few centimeters and are primarily employed to produce X-ray images of individual or a few neighboring teeth.

In contrast to intraoral exposure, with which the X-ray radiation sensor is in the mouth of the patient, in the case of a so-called panorama exposure, the head of the patient is located between the X-ray radiation generator and the sensor. In this X-ray technique, the X-ray head with the radiation generator is moved around to the head of the patient, during which the jaw region of the patient is continuously penetrated by the X-ray radiation, which, in turn, is detected by an X-ray radiation detector. Through the particular movement of the X-ray head, a so-called panorama exposure is produced, which is an overview representation of the teeth of the lower jaw and of the upper jaw of the patient. Such panorama exposures are particularly well-suited for recognizing faulty positioning of individual teeth.

Although the radiation exposure of the patient, both in the case of intraoral exposure and also in the case of panorama exposure, is relatively slight in comparison to the radiation exposure in the case of X-ray investigations of other regions of the body, in dental X-ray diagnosis there is also the responsibility to keep the radiation exposure as slight as possible. A significant prerequisite for this is that unnecessary repetition of faulty X-ray exposures, due to a false positioning of the sensor or a false directing of the X-ray head, are avoided. Consequently, there is a particular need for optimizing the direction and configuration of the X-ray head or the sensor element.

In the case of an intraoral use, the task lies in, on one hand, placing the sensor within the mouth in the desired position behind the tooth to be investigated and, on the other hand, directing the X-ray head centrally at the sensor. This is, on one hand, problematic because, with a closed mouth, the sensor cannot be recognized from the outside and, on the other hand, because the X-ray radiation is itself not visible, the dentist or the person carrying out the X-ray exposure cannot be certain whether or not the radiation is, in fact, directed at the desired region. In the case of carrying out a panorama exposure, another difficulty arises in that the X-ray head must, as far as possible, be moved around the head of the patient in a particular plane. If this plane is departed from during the movement of the X-ray head, the quality of the panorama exposure is significantly affected.

To facilitate directing the X-ray head when carrying out an intraoral exposure, it is known to date to use mechanical aids. For example, it is known to so configure the holder for the X-ray film or for the digital sensor so that a part of the holder projects from the mouth of the patient and indicates at what position within the mouth the sensor is located. Through such a configuration, the dentist can recognize at least on which region outside the head the X-ray radiation should be incident. However, there is still the problem that for the dentist it is not apparent whether or not the invisible X-ray radiation is actually incident on the desired region.

SUMMARY OF THE INVENTION

It is accordingly an object of the invention to provide an X-ray apparatus that overcomes the hereinafore-mentioned disadvantages of the heretofore-known devices of this general type and that improves directing the X-ray head when carrying out a dental X-ray investigation.

With the foregoing and other objects in view, there is provided, in accordance with the invention, an X-ray apparatus, including an X-ray head having an X-ray tube having forward end region, an X-ray radiation source for generating X-ray radiation to be directed at an object to be investigated, an optical device having an aiming device with an optical axis oriented substantially parallel to the generated X-ray radiation and to be directed at the object, the aiming device having a visible light source generating visible pilot radiation through the optical device at the object to be investigated, and a transparent exit region forming the forward end region of the X-ray tube for the X-ray radiation and the visible radiation exiting the X-ray tube, the transparent exit region of the X-ray tube being removable and receiving a tube extension in place of the removable transparent exit region.

The solution in accordance with the present invention lies in providing the X-ray apparatus additionally with an aiming device, the optical axis of which is directed at the object to be investigated, through an optical device, substantially parallel to the X-ray radiation. The aiming device may include, in particular, along with the X-ray radiation source, a further light source for generating a visible pilot radiation, which with the aid of the optical device, is directed parallel to the X-ray radiation at the object to be investigated.

With the aid of the pilot radiation, which may, for example, be laser radiation, optical information can be applied to the exterior of the object to be investigated. Such application permits a user to deduce on which region the X-ray radiation will exactly be incident. In the case of carrying out of an intraoral exposure, the remaining task for the dentist, thus, lies only in determining on which region at the exterior of the head of the patient the X-ray radiation should be incident so that the sensor located in the mouth will be exposed.

A further development of the present invention is concerned with the fact that upon carrying out of intraoral X-ray exposures, the X-ray head is disposed directly at the exterior of the head of the patient or very near thereto. Because the pilot radiation is only helpful for a dentist when it is also well observable, at least the forward end of the X-ray tube is formed to be transparent. Through such a configuration, the dentist can still recognize, even when the dentist places the X-ray head directly on the head of the patient, on which region the X-ray radiation will be incident.

The optical information generated with the aid of the pilot radiation may be of different nature in each case depending upon the kind of investigation to be carried out. In the case of an intraoral X-ray exposure, it is sufficient to generate information that designates the center of the incident X-ray radiation. For such a purpose, for example, the projection of a point, a circle—in the case of a ring-shaped pilot beam, or a cross, is sufficient. The employment of a ring-shaped pilot beam for the generation of a circle offers the advantage that a deduction can be made concerning the axial disposition of the target in comparison to the X-ray head because, in the case of non-perpendicular incidence of the pilot radiation, the ring-shaped pilot beam would be distorted to an ellipse.

If a panorama exposure is to be carried out, the pilot radiation is, preferably, so effected to project a horizontally directed line on the exterior of the head of the patient. The employment of a line is, in this case, of advantage because the plane in which the X-ray head will be moved around the head of the patient can be characterized. If, for example, previously it has been indicated with the aid of a face bow on the cheeks of the patient how the biting plane develops, with the aid of the pilot radiation, the plane of rotation of the X-ray head can be matched optimally to the biting plane and, therewith, optimization of the panorama exposure.

A further possibility lies also in creating a scale by employing of a plurality of parallel lines as pilot radiation. Such a configuration opens up the possibility of determining the spacing between the X-ray head and the head of the patient.

The aiming device projects the visible pilot radiation substantially as a light point on the object to be investigated and the X-ray radiation source and the aiming device coaxially direct the X-ray radiation and the visible pilot radiation.

In accordance with another feature of the invention, the aiming device projects the visible pilot radiation substantially as a line on the object to be investigated, the X-ray radiation source has a central axis on which the X-ray radiation is generated and the line of the visible pilot radiation intersects the central axis.

In accordance with a further feature of the invention, the aiming device images the visible pilot radiation substantially as a horizontally directed line.

In accordance with an added feature of the invention, the X-ray head executes a rotation movement and the line defines a plane of rotation for the rotation movement of the X-ray head containing the X-ray radiation source.

In accordance with an additional feature of the invention, the aiming device projects a plurality of parallel lines onto the object to be investigated.

In accordance with yet another feature of the invention, the light source for the pilot radiation, preferably, a laser that emits light in the visible region, for example, a HeNe laser or a laser diode, is usually likewise disposed in the X-ray head, which already contains the X-ray source for the generation of the X-ray radiation. As an optical device, which is intended to direct the laser radiation in substance parallel to the X-ray radiation, in accordance with yet a further feature of the invention, there is preferably employed a beam splitter disposed in the beam path of the X-ray radiation, which acts in a reflecting manner for the pilot radiation but, in contrast, for the X-ray radiation is in substance transparent. A material that manifests this required characteristic is, for example, aluminum.

In accordance with yet an added feature of the invention, the beam splitter substantially reflects light in a visible wavelength range and is substantially transparent for the X-ray radiation.

In accordance with yet an additional feature of the invention, the beam splitter filters the generated X-ray radiation.

In accordance with again another feature of the invention, the optical device includes a beam splitter disposed in a beam path of the X-ray radiation, the aiming device projects the visible pilot radiation to the beam splitter at a point of incidence; and the beam splitter is one of domed and curved in a region of the point of incidence of the pilot radiation.

In accordance with again a further feature of the invention, the aiming device projects the visible pilot radiation onto the object to be investigated in a marking having a shape that is one of a substantially circular and substantially in a cross and the X-ray radiation source and the aiming device coaxially direct the X-ray radiation and the visible pilot radiation.

In accordance with again an added feature of the invention, there are provided a holder for an X-ray radiation detection sensor to be disposed in a mouth of a patient, a targeting device disposed outside the mouth of the patient and having a targeting marking indicating a point of incidence for the pilot radiation, and an alignment device connecting the holder in a defined manner with the targeting device.

In accordance with again an additional feature of the invention, the aiming device projects red pilot radiation.

In accordance with still another feature of the invention, the light source generating the pilot radiation is one of a HeNe laser and a diode laser.

In accordance with still a further feature of the invention, the transparent exit region is of Poly Methyl Meth Acrilate (PMMA) also referred to under the trade name PLEXIGLAS®.

In accordance with still an added feature of the invention, the pilot radiation indicates an operational condition of at least one of the X-ray head, the X-ray radiation source, and an image detection device.

In accordance with still an additional feature of the invention, the aiming device is activated to generate the pilot radiation only when at least one of the X-ray head, the X-ray radiation source, and the image detection device are ready for use.

In accordance with an advantageous development of the invention, the light source for the pilot radiation is not permanently switched on, but can be activated only under certain conditions and after the carrying out of an X-ray exposure is switched off at certain time points or under certain conditions. As will be explained below in more detail, through such a configuration, possibilities are provided for the dentist or for another person carrying out the X-ray exposure to determine in a simple or rapid manner whether or not the X-ray apparatus is ready for use, whether or not the film was correctly exposed, or whether or not the patient has moved.

In accordance with another feature of the invention, the aiming device keeps the pilot radiation activated for a given overrun time after an activation of the X-ray radiation source occurs.

The optical device, that is, the beam splitter, can also be employed for the purpose of directing an optical observation system on the axis of the X-ray radiation. This is, for example, of interest when it is of use, in the evaluation of the X-ray exposure, to view the region to be irradiated from the direction of the X-ray radiation, thereby, to be better able to monitor the location of incidence and lateral extension of the area of irradiation. For example, for such a purpose, there may be employed a camera or other observation device that, with the aid of the beam splitter, can be directed at the area irradiated by the X-ray radiation.

In accordance with a further feature of the invention, there is provided an optical observation system for detecting a region of incidence of the pilot radiation.

In accordance with an added feature of the invention, the optical observation system obtains information with regard to spacing and an orientation of the object to be investigated based upon a distortion of the pilot radiation that is detected by the optical observation system upon the surface of the object to be investigated.

In accordance with an additional feature of the invention, program parameters for movement of the X-ray head are derived based upon the information regarding the spacing and the orientation of the object to be investigated.

In accordance with yet another feature of the invention, the X-ray radiation source generates the X-ray radiation in an X-ray beam having an axis and the optical device has an optical observation system and directs the optical observation system on the axis of the X-ray beam.

In accordance with yet a further feature of the invention, the optical observation system is a camera.

In accordance with yet an added feature of the invention, the X-ray head is a dental X-ray head.

In accordance with yet an additional feature of the invention, the transparent exit region is of a clear plastic.

In accordance with again another feature of the invention, the optical device has an image detection device and the pilot radiation emitted by the aiming device indicates an operational condition of at least one of the X-ray head, the X-ray radiation source, and the image detection device.

In accordance with again a further feature of the invention, the aiming device is activated to generate the pilot radiation only when each of the X-ray head, the X-ray radiation source, and the image detection device are ready for use.

In accordance with a concomitant feature of the invention, the X-ray radiation has an axis, an optical observation system is connected to the optical device, and the optical device directs the optical observation system on the axis of the X-ray radiation.

With the objects of the invention in view, there is also provided an X-ray apparatus, including an X-ray head having an X-ray tube having forward end region, an X-ray radiation source generating X-ray radiation through the X-ray tube to be directed at an object to be investigated, an optical aiming device having a visible light source generating visible pilot radiation through the X-ray tube along an optical axis oriented substantially parallel to the X-ray radiation and at the object to be investigated, and at least a portion of the forward end region of the X-ray tube being a transparent removable exit region for the X-ray and visible radiation exiting the X-ray tube, the exit region being shaped to receive a tube extension in place of the portion.

With the objects of the invention in view, there is also provided an X-ray apparatus, including an X-ray head having an X-ray tube having forward end region, an X-ray radiation source generating X-ray radiation through the X-ray tube to be directed at an object to be investigated, an optical aiming device having a visible light source generating visible pilot radiation through the X-ray tube along an optical axis oriented substantially parallel to the X-ray radiation and at the object to be investigated, and at least a portion of the forward end region of the X-ray tube being an exit region for the X-ray and visible radiation exiting the X-ray tube, the exit region being transparent and removable; and a tube extension shaped to replace the exit region when removed.

Other features that are considered as characteristic for the invention are set forth in the appended claims.

Although the invention is illustrated and described herein as embodied in an X-Ray apparatus, it is, nevertheless, not intended to be limited to the details shown because various modifications and structural changes may be made therein without departing from the spirit of the invention and within the scope and range of equivalents of the claims.

The construction and method of operation of the invention, however, together with additional objects and advantages thereof, will be best understood from the following description of specific embodiments when read in connection with the accompanying drawings.

DESCRIPTION OF THE PREFERRED EMBODIMENTS

Figure 1:
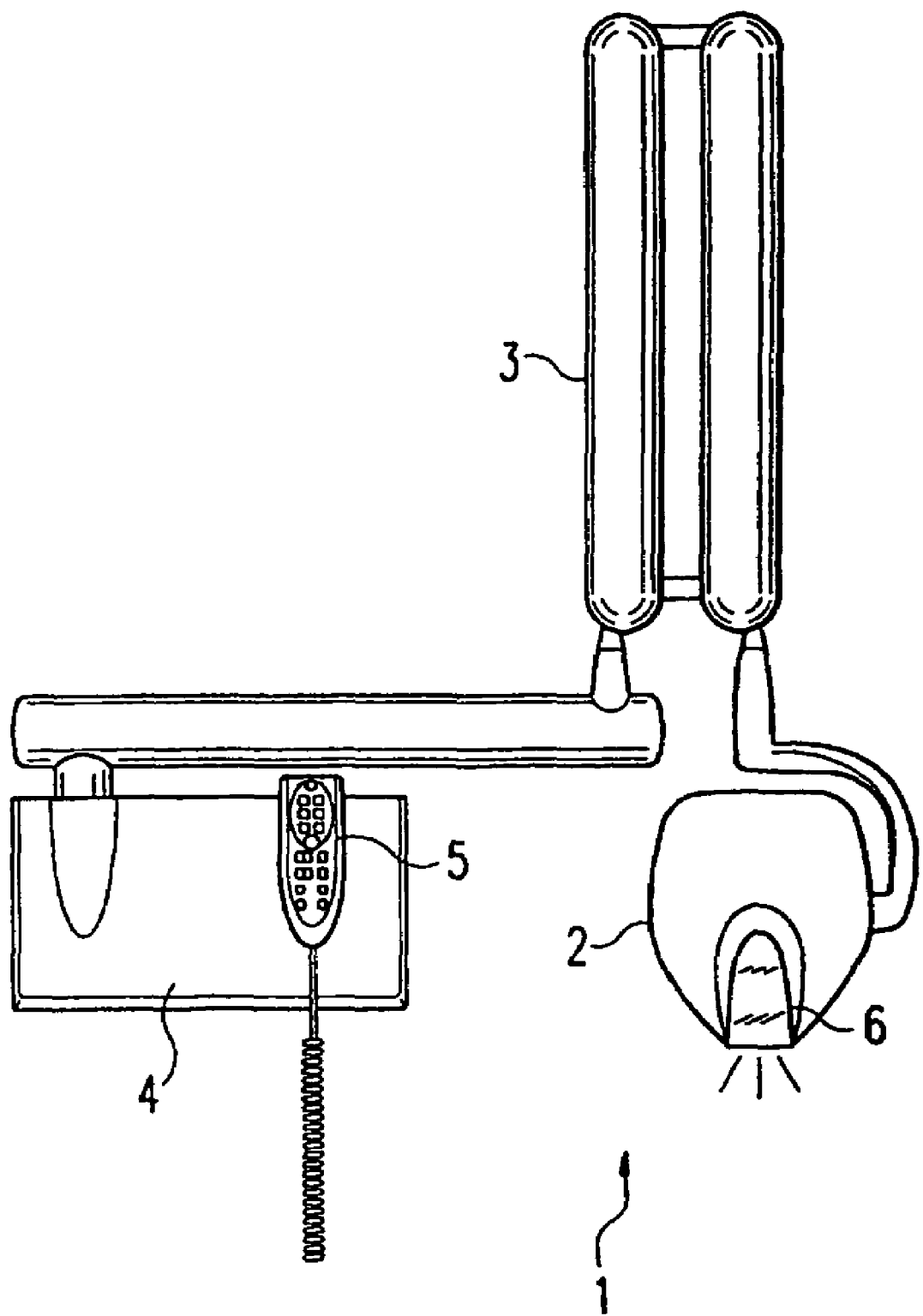
FIG. 1 is a fragmentary, side elevational view of a dental X-ray apparatus according to the invention.

Referring now to the figures of the drawings in detail and first, particularly to FIG. 1 thereof, there is shown a main component of the X-ray apparatus 1 and an X-ray head 2 containing the X-ray light source, which is connected moveably with a central unit 4 of the X-ray apparatus 1 through a framework 3 of a mounting. The mounting of the X-ray head 2 is such that it can be pivoted or displaced in as many degrees of freedom as possible and, thus, can be put to use in a flexible manner. The illustrated mounting is provided, in particular, for carrying out intraoral X-ray exposures because, with this exposure method, the X-ray head 2 is not moved during an exposure. In the case of so-called panorama exposures, in contrast, the X-ray head 2 is pivoted around a particular axis, which must be effected automatically to achieve a satisfactory image quality. The configuration for guided movement of the X-ray head 2, necessary for this purpose, is not illustrated in FIG. 1.

The central unit 4 contains the main control elements that are needed for control of the X-ray head 2 or the X-ray radiation source disposed therein. A further component of the central unit 4 is an input apparatus 5, through which the main parameters (for example, the radiation time, radiation duration, tube current (mA), tube voltage (kV) or the like) for carrying out the X-ray investigation can be input. Based upon this input, the central unit 4 generates control signals that are transmitted to the X-ray radiation source disposed in the X-ray head 2 through lines that run within the framework 3. The X-ray radiation generated in response is emitted through a tube 6 in the forward radiation exit region of the X-ray head 2. As will be explained in more detail below, the X-ray tube 6 is formed to be transparent at least in its forward region to open up the possibility for the dentist to use the assistance provided by the pilot radiation. For example, the X-ray tube 6 may be of PLEXIGLAS®.

Figure 2:
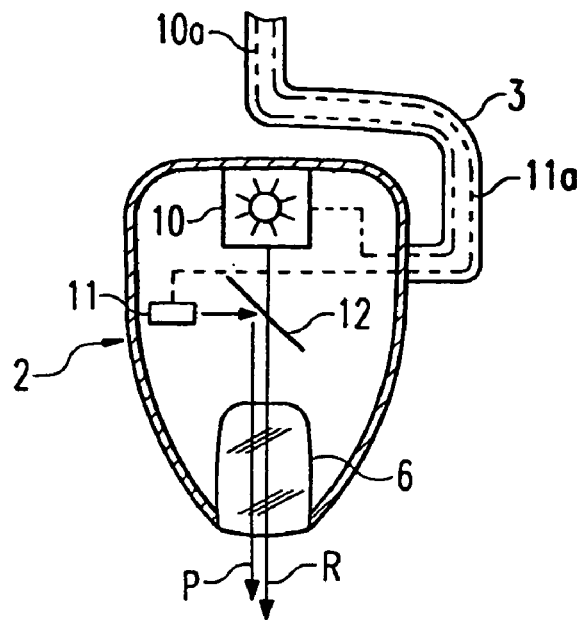
FIG. 2 is a diagrammatic, partially hidden and partially cross-sectional view of various light sources within an X-ray head of FIG. 1 and paths of the radiations thereof.

FIG. 2 shows schematically the internal construction of the X-ray head 2, which has, on one hand, the X-ray radiation source 10 for the generation of the X-ray radiation R and, on the other hand, an aiming device including a pilot radiation light source 11 and a beam splitter 12, which aiming device indicates the direction of the X-ray radiation R with the aid of a pilot beam P. Both the X-ray radiation source 10 and also the pilot radiation source 11 are controlled by the central unit 4 of the X-ray apparatus illustrated in FIG. 1 and, for this purpose, are connected with the central unit 4 through two lines 10a and 11a running in the framework 3.

Because the pilot radiation P offers the dentist optical assistance in directing the X-ray head 2 towards the object to be investigated, the pilot radiation P must be visible. Preferably, there is employed, for the visible radiation, a laser radiation in the red range. For example, there could be employed as light source 11 for the pilot radiation a helium-neon (HeNe) laser or a laser diode.

Directing of the X-ray head 2 with the aid of the pilot ray P is simplified the more accurately the X-ray radiation R and the pilot radiation P are aligned with one another. Preferably, the two radiations are directed axially of one another; a certain assistance is, however, also achieved where they are at least parallel to one another or solely deviate from one another with a small angle.

The coaxial alignment of the pilot radiation P to the X-ray radiation R is effected through a beam splitter 12, which is disposed in the radiation path of the X-ray radiation R. It is important here that the beam splitter 12 is of a material through which the X-ray radiation R can simply penetrate. In contrast, the pilot beam P is reflected by the beam splitter 12. For this purpose it is possible, for example, to realize the beam splitter 12 with a flat aluminum plate because aluminum has the desired characteristics. For the case that the beam splitter 12 is completely planar, the laser beam P emitted from the pilot radiation source 11 is projected point-like onto the surface of the object to be investigated and this point, then, represents the center of the X-ray radiation R.

It is to be remarked that the application of the beam splitter 12 in the X-ray radiation path can, due to the so-called inherent filtration associated therewith, also be exploited for hardening the X-ray radiation, whereby the scattered radiation thereby arising is absorbed within the interior of the X-ray head. Here, it is of advantage that aluminum is in any event employed for inherent filtration of X-ray radiation so that, with a corresponding setting of the material thickness of the mirror or beam splitter, inherent filtration can be brought about. The inherent filtration characteristics and, thereby the technical data of the apparatus remain unaltered.

Figure 3:
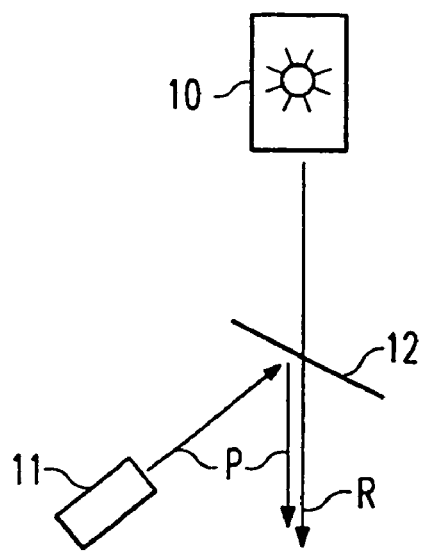
FIG. 3 is a diagrammatic illustration of an alternative configuration for coupling in pilot radiation according to the invention.

FIG. 3 shows a configuration of the X-ray radiation source 10, the light source 11 for the pilot beam P, and an alternative beam splitter 12 configuration as compared to FIG. 2. This beam splitter 12 differs in that the beam splitter 12 is not disposed at a 45° angle to the path of the X-ray radiation R. With regard to the manner of functioning of the beam splitter 12, there arise however no differences to the configuration of FIG. 2.

The assistance obtained through the employment of the pilot radiation for the dentist in the directing of the X-ray head will be explained below with reference to FIGS. 4 and 5.

Figure 4:
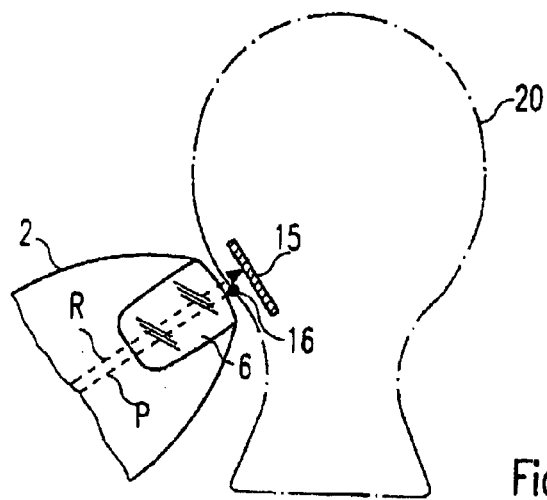
FIG. 4 is a fragmentary, diagrammatic and partially hidden view of a variant of the X-ray head of FIG. 1 and assistance provided by the pilot radiation according to the invention in the case of an intraoral exposure.

FIG. 4 shows the case of application for an intraoral X-ray exposure, in which an X-ray radiation sensitive sensor 15 is disposed in the mouth of a schematically illustrated head 20 of a patient. In this case of investigation, it is necessary to so direct the X-ray head 2 that the X-ray radiation R is incident as optimally as possible on the sensor 15.

The optimal direction is facilitated in accordance with the present invention by the pilot radiation P generating a marking 16 on the exterior of the head 20, the marking 16 clearly indicating in which region or at which position the X-ray radiation R will be incident on the head 20 of the patient. For the dentist, the problems are, thus, reduced exclusively to determining the necessary position on the exterior of head 20 of the patient that is needed to fully strike the sensor 15 disposed within the mouth. In this case, it is particularly of advantage that at least the forward region of the tube 6 of the X-ray head 2 is transparent because, even in the case that the X-ray head 2 is placed directly on the exterior of the head 20 of the patient, the position 16 at which the pilot ray P is incident is still recognizable. Also for the case that the X-ray tube 6 projects with respect to the housing of the X-ray head 2, it is advantageous to configure the X-ray tube 6 to be transparent to be able to optimally exploit the assistance of the pilot radiation.

In accordance with a further development, the transparent part of the X-ray tube 6 can be removable. Then, there is a possibility of installing a tube extension 8, for example. Also in this variant, at least a forward end region of the tube can be transparent, for example, the transparent part could be put in place at the forward end after the installation of the extension 8 to be able to exploit the assistance made available by the pilot beam P.

A further facilitation of the directing of the X-ray head 2 could, moreover, also be achieved in that the holder for the sensor 15 is combined with a non-illustrated mechanical targeting device, which, due to the fact that it is connected in a defined manner with the holder for the sensor 15, with the aid of an aligning device, it clearly defines a region outside the head of the patient 20 upon which the X-ray radiation R must be incident in order to expose the sensor 15. If such a holder is additionally provided with a target marking, a correct alignment of the X-ray head 2 could, for example, thereby be indicated because the pilot beam P is incident on the target marking. The quality of the X-ray exposure obtained through such a configuration is, therewith, significantly improved. At the same time, it is ensured that the exposure need not be repeated due to a faulty alignment of the X-ray head 2. The target marking in this case represents a so-called "bull's eye" referring to the sensor or the X-ray film, through which the correct position or alignment of the X-ray beam can be monitored.

Figure 5:
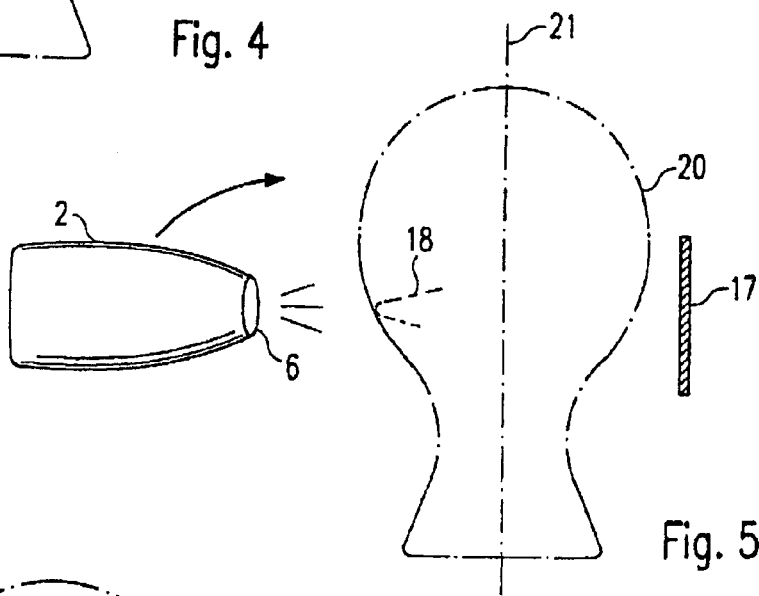
FIG. 5 is a diagrammatic and partially hidden view of another variant of the X-ray head of FIG. 1 and assistance provided by the pilot radiation according to the Invention in the case of a panorama exposure.
Figure 6:
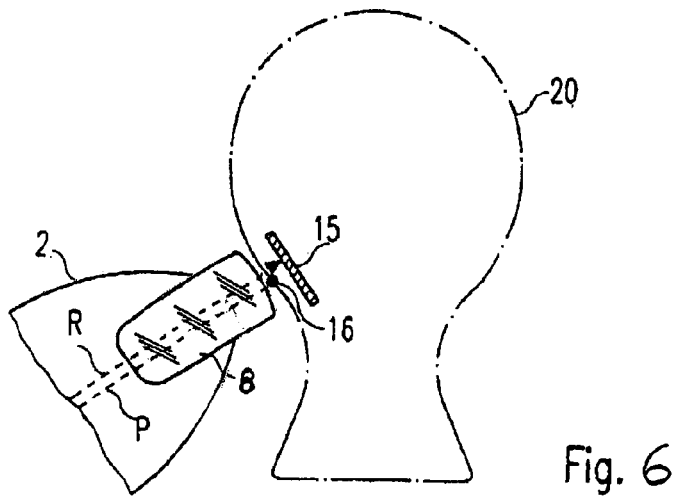
FIG. 6 is a fragmentary, diagrammatic and partially hidden view of a variant of the X-ray head of FIG. 1, where the tube has been replaced with a tube extension.

FIG. 5 shows a further exemplary embodiment of the aiming device in accordance with the invention. In the case of FIG. 5, a so-called panorama exposure is produced, in which the X-ray head 2 is pivoted around the central axis 21 of the head 20 of the patient. At the same time, the sensor 17 lying on the opposite side of the head 20 of the patient is correspondingly moved in a defined movement, through which, overall, an overview exposure of the teeth of the upper jaw and of the lower jaw is obtained.

A problem in the case of this exposure technique lies in that the X-ray head 2 should, as far as possible, be moved in the biting plane of the patient to obtain an optimal imaging result. The aiming device in accordance with the invention can be so constituted for this case that it does not generate a single point on the exterior of the head 20 of the patient, coaxial to the X-ray radiation but, instead, generates a horizontally directed line 18 intersecting the central axis of the X-ray radiation. The line 18 thereby shows in which plane the X-ray head 2 will turn. For the dentist, the task of orienting the X-ray head 2 is reduced to bringing the line 18 indicated by the pilot radiation into concert with the biting plane of the patient 20. This can, however, be effected in a simple manner in that, previously, with the employment of a face bow, it is indicated or marked on the cheeks of the patient how the biting plane develops. In this step, the dentist determines the development or the configuration of the so-called "Frankfurt horizontal plane". The X-ray head 2 must, in the end, merely be so directed that the line 18 generated by the pilot radiation strikes the marking.

The generation of the line 18, instead of an individual point, with the aid of the pilot radiation can be effected in a particularly simple manner by forming the beam splitter shown in FIG. 2 not to be planar but, instead, slightly domed. Through this, there is attained a fanning out of the pilot beam, through which the desired line 18 can be generated.

Instead of projecting a simple point or a line with the aid of the pilot beam, other markings may, however, be projected, which make possible a suitable directing of the X-ray head towards the head of the patient. For example, a ring-shaped or cross-shaped pilot beam can also be generated that runs coaxial to the X-ray radiation. Another possibility lies in projecting a plurality of parallel running lines and, through this, providing a scale, which opens up the possibility of determining the spacing between the X-ray light source and the head of the patient.

Finally, it should be noted that the pilot radiation, as well as being an aid for the directing of the X-ray head, can also be employed for the purpose of indicating to the dentist an operating condition of the X-ray apparatus. Advantageously, the pilot beam is, namely, not permanently activated, but only when the complete X-ray system, that is both the X-ray apparatus and also any digital image detection equipment involved, is ready for use. Usually, before an activation of the X-ray radiation source, the dentist carries out a brief check whether or not the exposure system is ready for use because, otherwise, the patient would be unnecessarily exposed to radiation. A corresponding check is, in the case of the advantageous development of the invention, superfluous because it is automatically apparent for the dentist based upon the presence or absence of the pilot radiation in the aligning of the X-ray head, whether or not the overall system is ready for use. To indicate a fault in operation of the system, the pilot radiation could, for example, also be modulated so that the marking appearing on the face of the patient flashes.

After carrying out the X-ray exposure, the pilot beam is manually or automatically switched off, whereby, however, advantageously it remains activated for a certain overrun time. This so-called overrun light control offers the possibility that the dentist can still check, after the exposure, whether the patient has moved his head in the interim or the directing of the X-ray head at the head of the patient has changed in the interim. This overrun light control is of advantage particularly when a classical X-ray radiation detector, that is an X-ray film, is employed because the dentist can determine, before the development of the film, if the exposure was faulty and, if so, require the procedure to be repeated.

The beam splitter can also be employed to direct a non-illustrated optical observation system on the axis of the X-ray beam. This is, for example, then of interest if, in the evaluation of the X-ray exposure, it is of use to view the irradiated zone from the direction of the X-ray beam to thereby be better able to monitor the location of incidence and lateral extension of the irradiation area. For example, for such a purpose, there may be employed a camera or other observation device, which with the aid of the beam splitter is directed at the zone irradiated by the X-ray radiation.

Another possibility, which is particularly of use for the production of panorama exposures, lies in fanning out the pilot beam and observing the area of incidence of the pilot radiation at the same time with an observation device or a camera. From the distortion of the fanned out pilot radiation on the face of the patient, there can then be determined the spacing and the direction of the head of the patient and, from this, corresponding program parameters for the movement of the X-ray head automatically derived. The combination of the pilot radiation with an optical observation device thus opens up the possibility of realizing a virtually completely self-running exposure procedure. The information obtained with the aid of the camera can also be used to derive instructions for positioning the head of the patient.

The present invention, thus, provides an aid that makes possible a simple and reliable directing of the X-ray head of an X-ray apparatus at the desired position. The measures necessary for this purpose require no high costs and contribute to a significant increase of exposure quality. The employment of the pilot beam offers, beyond this, also the possibility of indicating to a user of the X-ray apparatus in a simple manner whether the system is ready for use or system faults are present, which faults endanger the carrying out of the X-ray investigation.

We claim:
1. An X-ray apparatus, comprising:
an X-ray head having:
 an X-ray tube having a forward end region;
 an X-ray radiation source selectively generating X-ray radiation along a central X-ray axis at an object to be investigated;
 an optical device having an aiming device with an optical axis oriented substantially parallel to the generated X-ray radiation and to be directed at the object, said aiming device having a visible light source generating visible pilot radiation through said optical device at the object to be investigated;
 a transparent exit region having a given length along said central X-ray axis and forming said forward end region of said X-ray tube for the X-ray radiation and the visible radiation exiting said X-ray tube, said transparent exit region of said X-ray tube being removable; and a tube extension having a forward end region and a length along said central X-ray axis greater than said given length, said tube extension replace said transparent exit region after said transparent exit region is removed, said transparent exit region shaped to connect at said forward end region of said tube extension after installation of said tube extension at said X-ray tube to, thereby, extend said length of said tube extension along said central X-ray axis.

2. The X-ray apparatus according to claim 1, wherein said optical device includes a beam splitter disposed in a beam path of the generated X-ray radiation.

3. The X-ray apparatus according to claim 2, wherein said beam splitter substantially reflects light in a visible wavelength range and is substantially transparent for the X-ray radiation.

4. The X-ray apparatus according to claim 3, wherein said beam splitter is of aluminum.

5. The X-ray apparatus according to claim 2, wherein said beam splitter filters the generated X-ray radiation.

6. The X-ray apparatus according to claim 1, wherein:
said aiming device projects the visible pilot radiation substantially as a light point on the object to be investigated; and
said X-ray radiation source and said aiming device coaxially direct the X-ray radiation and the visible pilot radiation.

7. The X-ray apparatus according to claim 1, wherein:
said aiming device projects the visible pilot radiation substantially as a line on the object to be investigated;
said X-ray radiation source has a central axis on which the X-ray radiation is generated; and
said line of the visible pilot radiation intersects said central axis.

8. The X-ray apparatus according to claim 7, wherein said aiming device images the visible pilot radiation substantially as a horizontally directed line.

9. The X-ray apparatus according to claim 7, wherein:
said X-ray head executes a rotation movement; and
said line defines a plane of rotation for said rotation movement of said X-ray head containing said X-ray radiation source.

10. The X-ray apparatus according to claim 7, wherein said aiming device projects a plurality of parallel lines onto the object to be investigated.

11. The X-ray apparatus according to claim 7, wherein:
said optical device includes a beam splitter disposed in a beam path of the X-ray radiation;
said aiming device projects the visible pilot radiation to said beam splitter at a point of incidence; and
said beam splitter is one of domed and curved in a region of said point of incidence of the pilot radiation.

12. The X-ray apparatus according to claim 1, wherein:
said aiming device projects the visible pilot radiation onto the object to be investigated in a marking having a shape that is one of substantially circular and substantially in a cross; and
said X-ray radiation source and said aiming device coaxially direct the X-ray radiation and the visible pilot radiation.

13. The X-ray apparatus according to claim 1, further comprising:
a holder for an X-ray radiation detection sensor to be disposed in a mouth of a patient;
a targeting device disposed outside the mouth of the patient and having a targeting marking indicating a point of incidence for the pilot radiation; and
an alignment device connecting said holder in a defined manner with said targeting device.

14. The X-ray apparatus according to claim 1, wherein said aiming device projects red pilot radiation.

15. The X-ray apparatus according to claim 14, wherein said visible light source generating the visible pilot radiation is one of a HeNe laser and a diode laser.

16. The X-ray apparatus according to claim 1, wherein said transparent exit region is of Poly Methyl Meth Acrilate.

17. The X-ray apparatus according to claim 1, wherein the visible pilot radiation indicates an operational condition of at least one of said X-ray head, said X-ray radiation source, and an image detection device.

18. The X-ray apparatus according to claim 17, wherein said aiming device is activated to generate the visible pilot radiation only when at least one of said X-ray head, said X-ray radiation source, and said image detection device are ready for use.

19. The X-ray apparatus according to claim 1, wherein said aiming device keeps the visible pilot radiation activated for a given overrun time after an activation of said X-ray radiation source occurs.

20. The X-ray apparatus according to claim 1, further comprising an optical observation system for detecting a region of incidence of the visible pilot radiation.

21. The X-ray apparatus according to claim 20, wherein said optical observation system obtains information with regard to spacing and an orientation of the object to be investigated based upon a distortion of the visible pilot radiation that is detected by the optical observation system upon a surface of the object to be investigated.

22. The X-ray apparatus according to claim 21, wherein program parameters for movement of said X-ray head are derived based upon said information regarding the spacing and the orientation of the object to be investigated.

23. The X-ray apparatus according to claim 1,
wherein said optical device has an optical observation system and directs said optical observation system on said central X-ray axis.

24. The X-ray apparatus according to claim 23, wherein said optical observation system is a camera.

25. The X-ray apparatus according to claim 1, wherein said X-ray head is a dental X-ray head.

26. The X-ray apparatus according to claim 1,
wherein said tube extension has a length different from said given length and interchangeably replaces said transparent exit region.

* * * * *